United States Patent [19]

Beckermann et al.

[11] Patent Number: 4,871,767

[45] Date of Patent: Oct. 3, 1989

[54] MEDICAMENT PREPARATIONS

[75] Inventors: Bernhard Beckermann; Hans-Dieter Dell, both of Bergisch-Gladbach; Harald Horstmann, Wuppertal; Reinhold Kraus, Cologne, all of Fed. Rep. of Germany

[73] Assignee: Troponwerke GmbH & Co, KG, Cologne, Fed. Rep. of Germany

[21] Appl. No.: 93,839

[22] Filed: Sep. 4, 1987

[30] Foreign Application Priority Data

Sep. 24, 1986 [DE] Fed. Rep. of Germany ....... 3632359

[51] Int. Cl.[4] ............................................ A01N 37/12
[52] U.S. Cl. .................................... 514/536; 514/936
[58] Field of Search .............................. 514/536, 936

[56] References Cited

U.S. PATENT DOCUMENTS

| 3,592,892 | 7/1971 | Nosler et al. | 514/936 |
|---|---|---|---|
| 4,205,089 | 5/1980 | Ladage et al. | 514/936 |
| 4,353,896 | 10/1982 | Levy | 514/936 |
| 4,652,557 | 3/1987 | Sandborn | 514/936 |

OTHER PUBLICATIONS

Jakobi et al., Drug Res. 27, 1326ff, (1977).

*Primary Examiner*—Paul Lieberman
*Assistant Examiner*—Willie J. Thompson
*Attorney, Agent, or Firm*—Sprung Horn Kramer & Woods

[57] ABSTRACT

Medicament preparations contain 2-(2-hydroxyethoxy)-ethyl N-($\alpha,\alpha,\alpha$-trifluoro-m-tolyl)-anthranilate and dimethyl sulphoxide.

5 Claims, No Drawings

MEDICAMENT PREPARATIONS

This invention relates to medicament preparations which contain 2-(2-hydroxy-ethoxy)-ethyl N-($\alpha,\alpha,\alpha$-trifluoro-m-tolyl)-anthranilate and dimethyl sulphoxide, a process for their preparation, and their use 2-(2-Hydroxy-ethoxy)-ethyl N-($\alpha,\alpha,\alpha$-trifluoro-m-tolyl)-anthranilate, named etofenamate according to INN, is a known active ingredient which has an antiinflammatory and antiphlogistic action and is used particularly in the form of gels (Arzneimittelforschung 27 (I), Special Edition 6b, 1299 to 1364 (1977)).

It is likewise known that dimethyl sulphoxide (DMSO) is capable of dragging medicaments dissolved in it through the skin into the bloodstream in a very short time (P. H. List, Arzneiformenlehre, 301, 4th edition, 1985).

However, a prediction of whether an auxiliary such as DMSO is suitable as a "schlepper" for medicaments is not possible and depends on the properties of the active ingredient (Drug Metabolism Reviews 14 (2), 220 (1983)). For example, with ibuprofen ointment (Muktadir, A. et al., Drug Dev.Ind. Pharm. 12 (1986) 2521-40) and solutions of methotrexat (McCullough, JL., J. Invest. Dermatol. 66 (1976), 103–107), kanamycin (Zverev, VM., Antibiotiki 26, (1981) 102-4) and gentanycin (Rubinstein, E., Experientia 36 (1980), 92–93) DMSO did not enhance or diminish the absorption of the drug.

A recognized test for determining the activity of antiphlogistics and antiinflammatories is the test on inflammation models (kaolin or carrageenan edema) in rat paws (Jakobi et al, Drug Res. 27, 1326 ff. (1977)), in which the action of the active ingredients is determined. Investigations have shown that medicament preparations of etofenamate and DMSO do not exhibit an increase in the action within the scope of the tests on rat paws.

The negative finding is confirmed in studies on other commercially available vehicles, for example laurocapran (Azone ®) in humans and animals. For example, in a cross over trial on 6 human volunteers with Rheumon gel vs. Rheumon gel with 1% Azone no significant enhancement of etofenamate absorption was found.

However, it has surprisingly been found that the absorption of etofenamate from medicaments containing etofenamate and DMSO is considerably increased in humans.

The invention relates to medicament preparations which contain etofenamate and dimethyl sulphoxide.

In the medicament preparations according to the invention, etofenamate and DMSO support themselves through a significant increase in absorption and more rapid absorption.

The medicament preparations according to the invention contain etofenamate and DMSO in the weight ratio 1:15 to 1:1, preferably 1:1.7 to 1:5.

The medicament preparations according to the invention can be applied in various forms. Topical applications, such as gels, creams, ointments, lotions, sprays and solutions, are preferred. In particular, gels and creams are preferred.

Gel-like medicament preparations according to the invention generally contain, in addition to etofenamate and DMSO, gel formers, such as adjuvants, bodying agents and additives which are known per se.

Adjuvants for the gel-like medicament preparations according to the invention may preferably be esters of monohydric and/or polyhydric alcohols of chain length $C_2$ to $C_{18}$ containing carboxylic acid components of chain length $C_6$ to $C_{18}$.

In this case, alcohol and carboxylic acid components are generally straight-chain or branched hydrocarbon radicals.

Alcohol components which may be mentioned are, in particular, monohydric alcohols having 2 to 6 carbon atoms and dihydric and polyhydric alcohols having 2 or 3 carbon atoms.

Carboxylic acid components which may be mentioned are carboxylic acids having a chain length of 12 to 16 carbon atoms.

Esters which may be mentioned as examples are: propylene glycol diesters, ethyl oleate, isopropyl myristate, isopropyl stearate, isopropyl palmitate, diisopropyladipate, diethyl sebacate, oleyl oleate, hexyl laurate and isooctyl stearate. In particular, diisopropyl adipate and isopropyl myristate are preferred.

Adjuvants for the medicament preparations according to the invention may, in addition, preferably be higher alcohols having 10 to 24 carbon atoms. The hydrocarbon radical may be straight-chain or branched. In particular, higher alcohols having 12 to 18 carbon atoms are preferred.

Higher alcohols which may be mentioned as examples are oleyl alcohol and 2-octyl-dodecanol. In particular, 2-octyl-dodecanol is preferred.

Medicament preparations may contain one or more, preferably 1 to 3, adjuvants.

Bodying agents which may be mentioned as examples are: highly disperse silica, for example Aerosil, hydrogel formers such as Veegum, polyglycols, such as polyethylene glycol and polypropylene glycol, pharmaceutically usable cellulose derivatives, such as methylcellulose, hydroxyethylcellulose and carboxymethylcellulose, carboxyvinyl polymers such as Carbopol ® (DE-A No. 2,641,210), alginic acid derivatives, such as salts of alginic acid and gum arabic.

Additives which may be mentioned are additives which promote blood flow or warming and scents.

Additives which promote blood flow or have a warming effect can be, for example, benzyl nicotinate, salicylic acid esters such as methyl salicylate, etherial oils, capsaicin, capsicum extract and N-vanillylnonanamide.

Scents which can be employed are the conventional pharmacologically acceptable substances, as long as they are compatible with the active ingredients and the adjuvants.

In addition, the gel-like medicament preparations according to the invention contain water and, if appropriate, lower alcohols (straight-chain or branched or aromatically substituted having 2 to 10 carbon atoms). Isopropanol, benzyl alcohol and ethanol are preferred.

Particularly preferred gel-like medicament preparations according to the invention generally contain 2 to 30, preferably 4 to 12, parts by weight of etofenamate, 10 to 30, preferably 15 to 20, parts by weight of DMSO, 5 to 80, preferably 10 to 40, parts by weight of adjuvants, 0.1 to 10, preferably 0.5 to 5, parts by weight of bodying agents, 0.5 to 5, preferably 1 to 3.5, parts by weight of additives, 15 to 80, preferably 20 to 40, parts by weight of water and 0 to 40, preferably 20 to 35, parts by weight of lower alcohols.

The gel-like medicament preparations according to the invention can be prepared as follows: etofenamate, DMSO, the adjuvants and the additives are dissolved in an alcohol, for example ethyl or isopropyl alcohol. The bodying agent is subsequently stirred into the solution. Gel formation is caused by neutralization by a basic substance (for example sodium hydroxide solution).

Particularly preferred cream-like medicament preparations according to the invention generally contain 20 to 30, preferably 5 to 15, parts by weight of etofenamate, 5 to 30, preferably 10 to 20, parts by weight of DMSO, 5 to 50, preferably 15 to 30, parts by weight of adjuvants, 0 to 20, preferably 1 to 8, parts by weight of bodying agents, 0 to 20, preferably 1 to 5, parts by weight of emulsifiers, 0.5 to 5, preferably 1 to 3.5, parts by weight of additives, 30 to 60, preferably 35 to 50, parts by weight of water and 1 to 5, preferably 1.5 to 3, parts by weight of lower alcohols.

Cream-like medicament preparations according to the invention generally contain, besides etofenamate and DMSO, cream formers, adjuvants and, if appropriate, bodying agents and/or emulsifiers and additives, such as substances which promote blood flow or have a warming effect, and also auxiliaries such as, for example, pleasantly smelling substances.

Adjuvants, bodying agents and additives can generally contain the same substances as the gels.

The emulsifiers which can be employed are one or more from the group comprising the ionogenic or non-ionogenic water-in-oil and oil-in-water emulsifiers.

Emulsifiers which are preferably employed are salts of higher fatty acids and bile acids, such as triethanolamine stearate, alkyl sulphates, such as Na lauryl sulphate, alkyl sulphonates, such as N-cetyl sulphonate, higher fatty alcohols, such as cetyl alcohol, lauryl alcohol and stearyl alcohol, sterine alcohols, such as cholesterol, fatty acid esters of polyhydric alcohols and polyols, such as ethylene monostearate, glycerol monooleate, sorbitan monolaurate, sorbitan trioleate, polyoxyethylene (20) sorbitan monolaurate, polyoxyethylene sorbitan hexaoleate, fatty alcohol ethers, such as polyoxyethylene lauryl ether and polyoxyethylene oleyl ether, fatty acid esters of saccharose, such as saccharose distearate, lecithin and derivatives, betaines and sulphobetaines, such as fatty acid amidoalkyl betaine and/or polyoxyethylene polyoxypropylene polymers such as Pluronics ®.

The cream preparations according to the invention are prepared by mixing etofenamate and DMSO with the other, optionally molten fat/wax emulsifier components, emulsifying the mixture with the aqueous phase of the preparation and subsequently subjecting the mixture to homogenization, for example using a rotor-stator device.

The homogenization temperature depends on the composition of the preparation and is generally in the range from about 35° and about 60° C.

Compared to conventional etofenamate preparations, the medicament preparations according to the invention have a considerable increase in action. They are therefore preferably used as analgesics and antiphlogistics.

EXAMPLE 1

In a randomized crossover experiment on 12 test subjects, significant differences were found with respect to absorption of etofenamate from cutaneously applicable etofenamate preparations, with and without DMSO. Both applications were carried out with the same active ingredient concentrations and application rates. The determination of the active ingredient level in human plasma was carried out by means of HPTLC [B. Beckermann et al., "Proc. 3rd Internat. Symposium on Instrumental High Performance Thin-Layer Chromatography" Würzburg/FRG 1985, published by Institute for Chromatography, D-6702 Bad Dürkheim/FRG, 15-24 (1985)].

The following differences were found between the two preparations:

time for maximum plasma level $t_{max}$ after DMSO-Etofenamate Gel (DEG) compared to Etofenamate Gel (EG) significantly shorter: 4.2 instead of 19 hours ($p < 0.001$)

maximum plasma level concentration $c_{max}$ after DEG twice as high as after EG ($p < 0.001$)

renal elimination after DEG in the first 12 and 24 hours post application significantly faster than after EG total absorption, measured from the area under the concentration time curve and from renal elimination, significantly greater after DEG than after EG (in each case $p < 0.001$) (paired t test, L. Sachs, Angewandte Statistik [Applied Statistics], pages 242-243 to (1984), Springer Verlag Berlin, 6th edition).

EXAMPLE 2

The absorption profile of DMSO-containing etofenamate preparations differs from that of DMSO-free preparations. It was possible to show that rapid cutaneous absorption of etofenamate in the presence of DMSO has a substantially identical time profile, for example rapid increase to peak plasma levels and decrease within one day to low values. In contrast to this, the DMSO metabolyte dimethyl sulphone ($DMSO_2$) only reaches maximum levels after more than one day, with a subsequent slow decrease.

The results on $DMSO/DMSO_2$ kinetics correspond to the data in K. H. Kolb et al., Ann. N.Y. Acad. Sci. 141, 85-95 (1967), inter alia.

In contrast, the substantially identical time profile of absorbed antiphlogistic (etofenamate) and DMSO is new.

It proves that DMSO has a positive vehicle function for etofenamate.

EXAMPLE 3

(comparison)

In the analgesia test in accordance with Randall-Selitto [L. D. Randall and J. J. Selitto, Arch. int. Pharmacodyn. 111, 409-419 (1957)], the activity of commercially available etofenamate gel (5% strength) and etofenamate gel containing 20% of DMSO was investigated comparatively on male Wistar II rats. In the case of applications of 50 mg of gel/kg of body weight in each case, the DMSO-containing etofenamate proved to have an equally strong analgesic action as the DMSO-free preparation.

This shows that no significant increase in etofenamate resorption or potentiation of the analgesic action by DMSO occurs in rats.

| Examples 4 to 9 (gels) | 1 | 2 | 3 | 4 | 5 |
|---|---|---|---|---|---|
| Etofenamate | 5.0 | 5.0 | 5.0 | 5.0 | 5.0 |
| DMSO | 20.0 | 20.0 | 20.0 | 20.0 | 20.0 |
| Diisopropyl adipate | 7.5 | 10.0 | — | — | 5.0 |
| Isopropyl pyristate | — | — | 5.0 | 7.5 | — |
| Isopropanol | 30.0 | 33.0 | 25.0 | 30.0 | 30.0 |
| Etherial oils | 0.2 | 0.2 | 0.2 | 0.2 | 0.2 |
| Water | 26.25 | 26.75 | 29.75 | 23.85 | 30.75 |
| Fatty alcohol polyglycol ether | 6.0 | — | 6.0 | 6.0 | — |
| Propylethylene glycol 400 | 3.0 | 3.0 | 3.0 | 3.0 | 3.0 |
| Propylene glycol | — | — | 3.0 | 3.0 | 4.0 |
| Hydroxypropyl-cellulose | — | — | 1.0 | — | — |
| Carboxyvinyl polymer | 1.3 | 1.3 | 1.3 | 1.3 | 1.3 |
| Sodium hydroxide solution, 10% strength | 0.75 | 0.75 | 0.75 | — | 0.75 |
| Ammonia solution, 28% strength | — | — | — | 0.15 | — |
|  | 100.0 | 100.0 | 100.0 | 100.0 | 100.0 |

| Examples 10 to 14 (cream) | | | | | |
|---|---|---|---|---|---|
| Example No. | 10 | 11 | 12 | 13 | 14 |
| Etofenamate | 5.0 | 5.0 | 5.0 | 5.0 | 5.0 |
| DMSO | 10.0 | 10.0 | 20.0 | 20.0 | 20.0 |
| Glycerol monodistearate | 12.0 | 12.0 | 9.0 | 11.0 | — |
| Glycerol monostearate | — | — | — | — | — |
| Diisopropyl adipate | 13.0 | 13.0 | 16.0 | — | — |
| Isopropyl lyristate | — | — | — | 16.0 | 17.0 |
| Cetyl alcohol | 3.4 | 3.4 | 3.4 | 1.4 | 3.4 |
| Myrj 59 | 5.0 | 5.0 | 5.0 | 5.0 | 5.0 |
| Trisodium citrate dihydrate | 0.5 | 0.5 | 0.5 | 0.5 | 0.5 |
| Sodium hydrogen citrate | 0.4 | 0.4 | 0.4 | 0.4 | 0.4 |
| Benzyl alcohol | 1.5 | 1.5 | 1.5 | 1.5 | 1.5 |
| Water | 49.2 | 49.2 | 39.2 | 39.2 | 37.2 |
|  | 100.0 | 100.0 | 100.0 | 100.0 | 100.0 |

It is understood that the specification and examples are illustrative but not limitative of the present invention and that other embodiments within the spirit and scope of the invention will suggest themselves to those skilled in the art.

We claim:

1. A medicament preparation comprising etofenamate and dimethyl sulphoxide, the ration of etofenamate to DMSO ranging from about 1:15 to 1:1.

2. A medicament preparation according to claim 1, including a gel former.

3. A medicament preparation according to claim 1, including a cream former.

4. A process for the preparation of a medicament preparation according to claim 2, comprising dissolving etofenamate and DMSO in an alcohol, adding a gel former, and then adding a base.

5. A process for the preparation of a medicament preparation according to claim 3, comprising adding etofenamate and DMSO to a cream former and then homogenizing.

* * * * *